United States Patent [19]
Reed

[11] Patent Number: 5,573,817
[45] Date of Patent: *Nov. 12, 1996

[54] METHOD AND APPARATUS FOR DELIVERING A SUBSTANCE INTO A MATERIAL

[76] Inventor: William C. Reed, 5753 Whistlewood Cir., Sarasota, Fla. 34232

[*] Notice: The portion of the term of this patent subsequent to Jan. 12, 2014, has been disclaimed.

[21] Appl. No.: 441,978

[22] Filed: May 16, 1995

Related U.S. Application Data

[63] Continuation-in-part of Ser. No. 180,432, Jan. 12, 1994, Pat. No. 5,415,900.

[51] Int. Cl.$^6$ ........................................... B05D 3/00
[52] U.S. Cl. .................. 427/561; 118/400; 118/623; 118/640; 118/712; 427/128; 427/132; 427/235; 427/239; 427/436; 427/443.2; 427/598
[58] Field of Search ...................... 427/561, 598, 427/128, 132, 235, 239, 436, 443.2; 118/712, 400, 623, 640

[56] References Cited

U.S. PATENT DOCUMENTS

| | | | |
|---|---|---|---|
| 4,122,209 | 10/1978 | Kinard | 427/598 |
| 5,209,946 | 5/1993 | Lowther | 427/598 X |
| 5,415,900 | 5/1995 | Reed | 427/598 X |

*Primary Examiner*—Bernard Pianalto
*Attorney, Agent, or Firm*—Malloy & Malloy, P.A.

[57] ABSTRACT

A method of delivering a substance into a material mass including the steps of measuring a quantity of a carrier fluid and a material to be delivered, mixing the carrier fluid and the material to be delivered, and subjecting the mixture to a magnetic influence for increasing a permeability and effectiveness thereof by affecting the organization of the molecules of the mixture. Finally the mixture is introduced to the material mass for penetrating therein and direct, substantial absorbing of the mixture by the material mass.

22 Claims, 2 Drawing Sheets

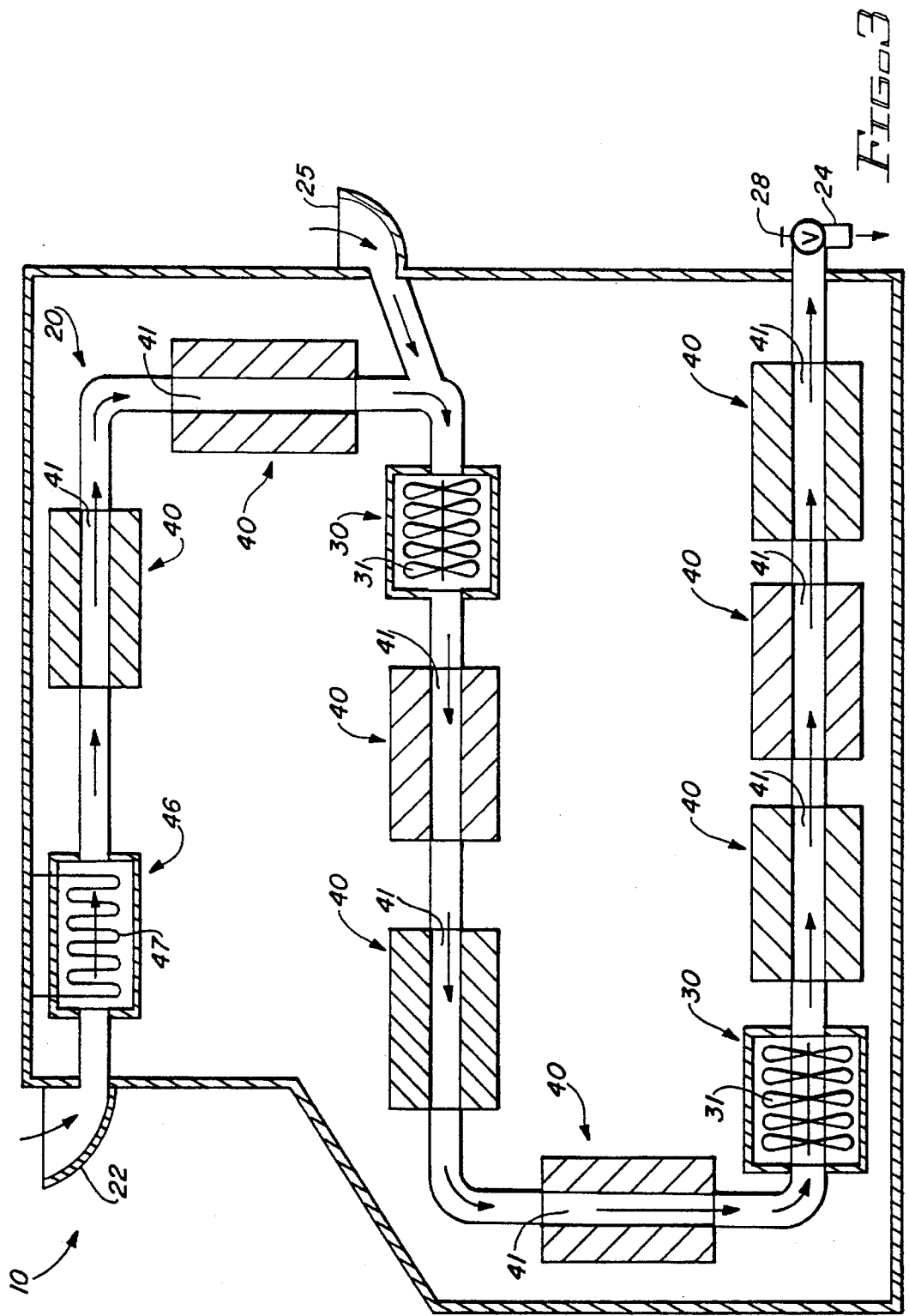

METHOD AND APPARATUS FOR DELIVERING A SUBSTANCE INTO A MATERIAL

This is a continuation-in-part of application Ser. No. 08/180,432, filed Jan. 12, 1994, U.S. Pat. No. 5,415,900.

BACKGROUND OF THE INVENTION

1. Field of the Invention

The present invention relates to a method of delivering a substance into a material mass, and a device for processing a substance to be introduced into a material mass, the substance being introduced substantially effectively by penetrating the substance through the surface and directly into the mass, rather than allowing the substance to minimally and gradually permeate or merely by providing a topical application of the substance to the surface(s) of the material mass.

2. Description of the Related Art

In a vast number of industries and applications, ranging from nutritional and medical applications to concrete or metal reinforcement, a beneficial substance must be introduced into a material mass so that its beneficial effects may be realized.

For example, in industries such as concrete, metal or wood reinforcement, there is a need to add strengthening chemicals throughout the interior of an object. In these circumstances, however, adding chemicals throughout the interior of a solid structure such as a concrete wall is substantially difficult because of the dense nature of the object. Accordingly, often only the exterior portions of the object receive the necessary treatment unless holes are drilled to the interior of the object. Drilling holes, however, is not appropriate for many objects, including antique articles or structures, because the holes themselves may reduce the structural integrity of the object, potentially leading to premature decay or detracting significantly from the appearance of the object. Moreover, even if holes are drilled into an object, strengthening chemicals will penetrate only as far as, and to the areas in communication with, the holes. Furthermore, due to the fast reacting nature of many strengthening chemicals, such chemicals are not able to be fully absorbed by the object before hardening.

As previously stated, in addition to industries in which dense objects need to be reinforced, the rapid and/or selective absorption of substances into material masses would be highly beneficial for other uses such as treating wood, deep cleansing material masses, introducing nutrients into plant structures, or any other application which requires rapid and directed absorption of a substance into a material mass.

Some other such examples involve the more effective absorption of nutrients and/or medicinal substances into humans and other animals. In particular, most such nutritional or medicinal substances cannot be fully absorbed into the necessary portions of the body before being eliminated, whether they are applied topically or digested internally. As such, the beneficial qualities are not utilized to their full capacity. Accordingly, providing a method or device which would enable more substantial and complete penetration into the body would be substantially beneficial.

The delivery method of the present invention is designed precisely to overcome many shortcomings found in existing methods of delivering necessary substances into material masses quickly.

SUMMARY OF THE INVENTION

The present invention is directed towards a method of delivering a substance into a material mass. In this method, initially, a quantity of a carrier fluid is measured, and at least one quantity of at least one material to be delivered is measured. Next the quantity of carrier fluid and the quantity of material to be delivered are mixed with one another. The resultant mixture is then subjected to a magnetic influence for polarizing the mixture and increasing a permeability and effectiveness thereof by affecting the organization of the molecules of the mixture. Finally, the treated mixture is introduced to the material mass for penetrating therein and direct, substantial absorbing thereof by the material mass.

The present invention is also directed towards a device for the magnetic processing of a substance to be delivered into a material mass. The device includes a fluid inlet structured to permit the introduction of a fluid composition therethrough, and a fluid outlet. Further the device includes magnetic means structured and disposed to subject the fluid composition to a magnetic influence for polarizing the fluid composition and increasing a permeability and effectiveness thereof by affecting the organization of the molecules of the mixture. Finally, the device includes recycling means structured and disposed to effect repeated subjecting of the fluid composition to the magnetic influence until the desired treated state is achieved.

The present invention takes advantage of the unique effects of magnetic induction which it is believed effects a linear molecular organization of a fluid substance to enhance its permeability (i.e., the ability of the fluid substance to penetrate) into a material mass in order to achieve rapid and complete penetration and absorption of such fluid substances into material masses of varying densities.

The purpose and function of magnetic inducement in the present invention is specifically directed to the rearrangement of fluid molecules from an agglomerated state to a more linear and organized state. As a result of this linear molecular organization produced by a magnetic influence, the fluid's permeability into a material mass is greatly enhanced, and penetration of the fluid through the surface and periphery of the material mass occurs much more readily than if the fluid's molecular organization had remained in an agglomerated state.

An additional advantage of fluid polarization effected by a magnetic influence instead of electrostatic means is that the charged polarity of the fluid molecules will be increased, thereby increasing the spaces between the individual fluid molecules through greater repellency. As a result of this increased charged polarity, the fluid molecules are separated to a greater extent so that the molecules are able to penetrate individually, rather than collectively, into a given material mass, thereby significantly enhancing the permeability of the fluid.

In addition, because fluid molecules charged by a magnetic influence become more separated, chemically reactive agents that are added to the fluids (which serve as carrier vehicles) attain a more uniform distribution amongst the fluid molecules. After the carrier fluids and chemically reactive agents therein are introduced into the material mass, the more uniform dispersion of the chemical agents in the carrier fluids results in an acceleration of the normal reaction time of such chemically reactive agents within the interior of the material mass. As such, the method of the present invention, on an initial level, can be used to more effectively introduce a substance in the form of an additive or a reactive agent into the carrier fluid material mass before the overall mixture is penetrated into a greater material mass such as the object to be treated.

Further, the method of the present invention is intended to deliver a substance into the interior, and not just onto the surface, of a material mass. The present invention utilizes a magnetic influence not merely as a substitute for an electrostatic means to charge fluid substances to opposite polarities, but as a means of effecting a linear organization and separation of the fluid molecules so as to greatly enhance the fluids' permeability through the surface and into the interior of a dense material mass such as a concrete structure.

It is an object of the present invention to provide a method of delivering a substance into a material mass which includes an enhanced permeability of the substance through the surface of the material mass and a rapid and complete absorption of the substance within the interior of the material mass, without the need to create openings in the mass through which the substance must be introduced.

A further object of the present invention is to provide a method of delivering a substance into a material mass which enables directed delivery of the substance to the interior of the material mass.

Also an object of the present invention is to provide a method of delivering a substance into a material mass which substantial increases the absorption of a material to be delivered into a carrier fluid, and which will substantially increase the effectiveness of a substance to be absorbed.

BRIEF DESCRIPTION OF THE DRAWING

For a fuller understanding of the nature of the present invention, reference should be had to the following detailed description taken in connection with the accompanying drawings in which:

FIG. 3 is a side cross-section view of yet another embodiment of the device of the present invention.

Like reference numerals refer to like parts throughout the several views of the drawings.

DETAILED DESCRIPTION OF THE PREFERRED EMBODIMENT

Figure 1:
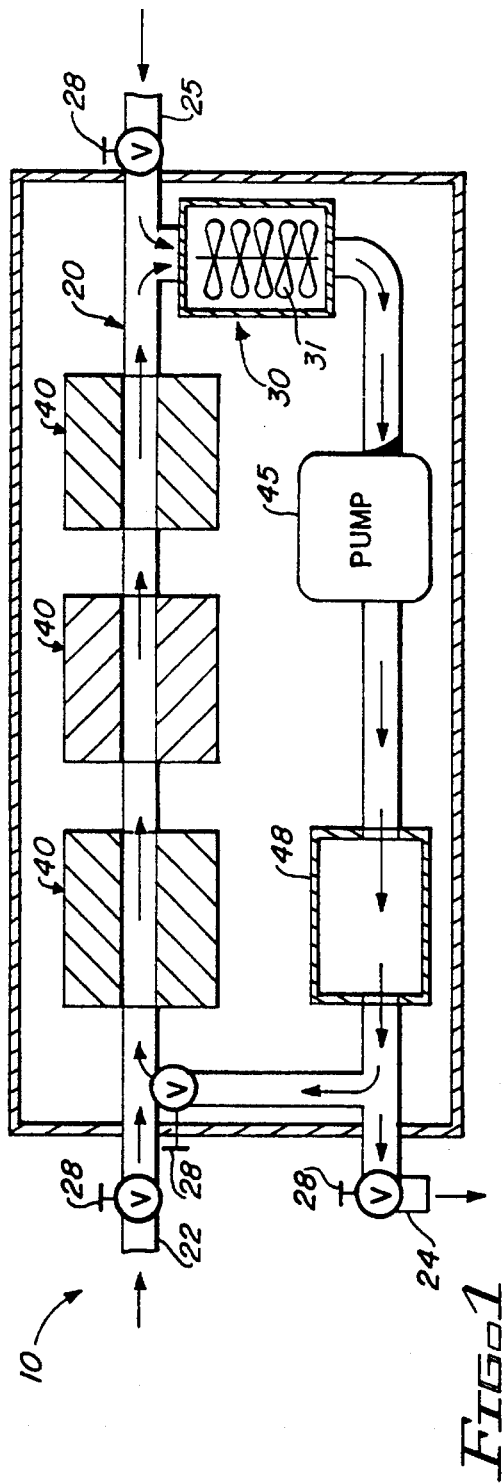
FIG. 1 is side cross-sectional view of a first embodiment of the device of the present invention.

The present invention is directed towards a method of delivering a substances into a material mass. Generally, when most substances are delivered to material masses the application of the substance must be substantial topical, at exposed surfaces, and will generally provide substantially slow if any absorption into the material mass. Accordingly, the method of the present invention seeks to provide rapid and substantial absorption into the surface of the material mass.

In the preferred embodiment, the method of the present invention involves the initial steps of measuring a quantity of a carrier fluid and measuring at least one quantity of at least one material to be delivered. For example, the preferred carrier fluid will generally be water because of its ready availability and its ability to absorb other materials therein. With regard to the material to be delivered, it will vary greatly depend upon a particular application of the method. For example, if the method is to be used to strengthen a concrete or metal structure so as substantially increase the compressive strength thereof and reinforce the structure, certain proprietary additives and strengthening chemicals which react specifically with the substance of the material mass are utilized. Similarly, in some medicinal purposes, such as for the application of an antibiotic or other curative balm, the medication material is added to the carrier fluid so that it will provide for more direct penetration to the portion of the body necessitating the treatment.

In the preferred embodiment, once the quantity of the carrier fluid and at least one quantity of at least one material to be delivered are measured, both substances are mixed with one another so as to provide a complete mixture therebetween.

Next, the resultant mixture is subjected to a magnetic influence which polarizes the mixture. Specifically, the magnetic influence will preferably be achieved utilizing the mono-pole permanent magnetic method developed by Peter Kulish in 1979, employing a magnetizing device such as that disclosed in U.S. Pat. No. 4,605,498. By subjecting the mixture to that magnetic influence, and preferably repeating or cycling the mixture through the magnetic influence a number of times, depending on the particular mixture being utilized, a permeability and effectiveness of the mixture will be substantially increased by the organization of the molecules of the mixture. As previously recited, the magnetic inducement will rearrange the fluid molecules of the mixture from an agglomerated state to a more linear and organized state. As a result of this linear molecular organization the fluid is much more permeable for penetration into the material mass as the organized and aligned molecules can more readily and effectively be absorbed through the open capillaries of the material mass for assimilation throughout the entire interior of the material mass.

In addition to affecting the organization of the overall mixture, the magnetic influence generally will also substantially increase the solubility of the material additive within the carrier solution such as water. Usually, carrier fluids will have a greater permeability than the material additive, especially after magnetically treated, such that by substantially combining the material additive with the carrier fluid the user can be assured of more even and complete dispersement of the necessary material additive within the material mass. Along these lines, and in an alternative embodiment, prior to mixing and/or measuring the material to be added, the carrier fluid can be subjected to the magnetic influence once or preferably a repeated number of times. Through this operation, the carrier fluid can become more receptive to total integration with the material to be added, and the further magnetic influencing of the mixture can have increased effectiveness to properly organize the molecules thereof.

Once the mixture has been magnetically influenced either once or a requisite number of additional times so as to achieve the desired integration and organization of the molecules of the mixture, that mixture is introduced to the material mass for penetration therein and direct, substantial absorbing of the mixture by the material mass. Because of the substantially increased permeability, the mixture can be applied directed to the surface without the need for more direct internal introduction. In the case of nutritional or medicinal substances to be taken internally, the organization of the molecules functions to ensure that the nutrients or medicinal substances are more greatly absorbed by the body prior to digestion thereof. Generally, with most such additives taken internally, a great portion of the beneficial substance is digested naturally by the body before it can be absorbed and be of use. As a result, utilizing the method of the present invention the amount of the nutrient or medical additive utilized by the body is greatly increased.

In additional embodiments of the method, the carrier fluid and/or the mixture of the carrier fluid and material to be added are subjected to a turbulent influence such as by the passage of the fluid through a plurality of mixing veins which agitate the fluid. As a result, the resultant mixture is more completely blended and will more effectively and uniformly be delivered to the material mass. Further, as additional embodiments, the carrier fluid and/or the mixture of the carrier fluid and the material to be delivered can be subjected to heating influences or sonic influences. In particular, some mixtures, depending upon the particular fluid and/or material to be delivered, are mixed more easily and more completely, so as to affect the appropriate organization for penetration, if subjected to additional influences. With regard to the heating influence, a heating coil can be introduced at some point so as to effectively heat the carrier fluid and/or mixture, especially in circumstances wherein the material to be delivered is not substantially soluble. Similarly, the sonic influence can function to effect appropriate blending without physical agitation, or as an addition to the physical agitation.

Finally, and yet another embodiment of the method of the present invention, the carrier fluid and material to be delivered are premixed into a single fluid material. Such is especially the case with nutritional materials, such as fruit juices and the like wherein the nutrients, or materials to be added, are already integral with the carrier fluid. In such a circumstance, the premixed and blended material is directly measured and subjected to the magnetic influence for organization of the molecules thereof to increase the permeability and effectiveness thereof prior to introduction to the material mass.

The method of the present invention will preferably be performed utilizing a device for the magnetic processing of a substance to be delivered into a material mass, generally indicated as 10. In particular, the device 10 will comprise a flow through path 20 wherethrough a fluid composition passes, a fluid inlet 22 being included to facilitate the introduction of the fluid composition. As previously recited, that fluid composition can either be the carrier fluid alone or a mixture of the carrier fluid and a material to be added.

Next, in a preferred embodiment, turbulating means 30 are included so as to agitate the fluid composition and further affect complete mixing thereof.

Disposed in fluid flow communication with the fluid inlet 22 and the preferred turbulating means 30 along the flow through path 20 are magnetic means 40. These magnetic means 40 are structured and disposed to subject the fluid composition to a magnetic influence for polarizing the fluid composition and increasing a permeability and effectiveness thereof by affecting the organization of the molecules of the mixture. In the preferred embodiment, the magnetic means 40 will include a central axis 41 where through the fluid composition passes. As such, the central axis 41 is disposed along the flow through path 20 in fluid flow communication with the fluid inlet 22. Additionally, the magnetic means 40 are structured to provide north and south magnetic fields and concentrate only one of the magnetic fields on the central axis 41 so as to provide magnetic treatment of the fluid composition located generally along the central axis and within the magnetic field. As previously recited, the magnetic means 40 will preferably be such as those disclosed in U.S. Pat. No. 4,605,498, issued to Peter Kulish, whose disclosure is hereby incorporated by reference.

Figure 2:
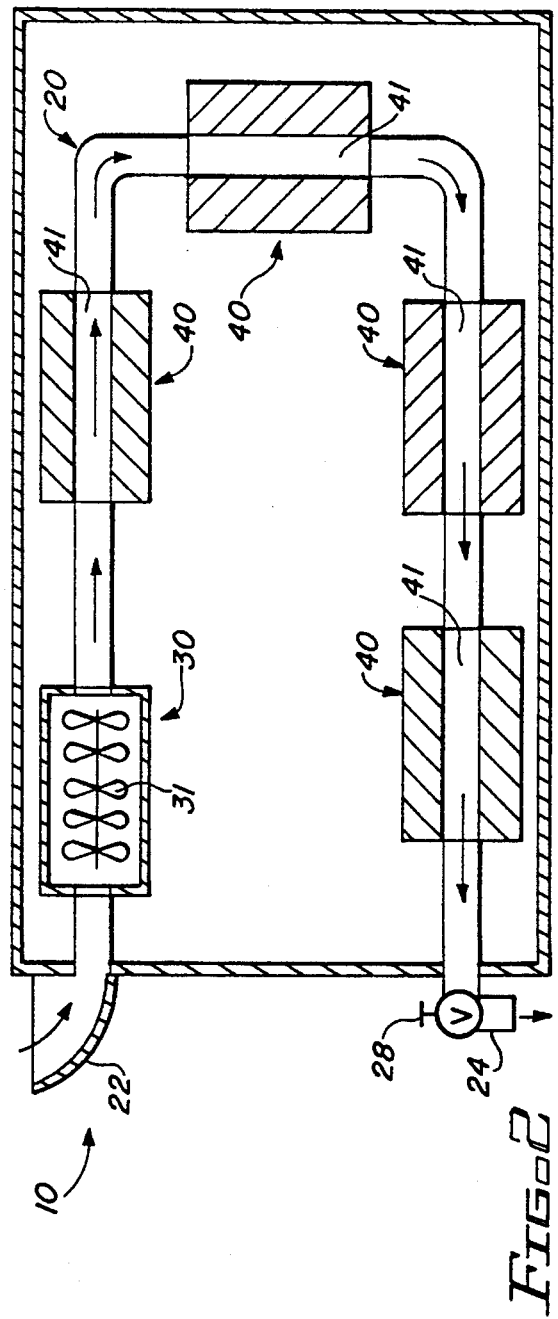
FIG. 2 is a side cross-sectional view of a second embodiment of the device of the present invention.

In the preferred embodiment, more than one magnetic means 40 will be included in line with one another such that the fluid composition passing through the device of the present invention can be subjected to sufficient magnetic influences to appropriately effect the organization of the molecules. Along these lines, in the preferred embodiment, recycling means are included so as to affect repeated subjecting of the fluid composition to the magnetic influence. For example, in one embodiment the recycling means include the positioning of a plurality showing FIGS. 2 and 3 of the magnetic means 40 in spaced apart distances from one another along the flow through path. Alternatively, however, as in FIG. 1 a pump 45 or other flow initiation means can be included so as to recycle the fluid composition back through the same one or more magnetic means on the flow through path 20. In such a circumstance a number of valves 28 can be included to control the direction of flow, and a computer control can designate the number of cycles.

So as to facilitate removal of the fluid composition, the device of the present invention also includes a fluid outlet 24 in the flow through path. As such, when the fluid composition has been sufficiently treated and/or cycled, it can be extracted from the device therethrough for use and introduction to the material mass.

In alternative embodiments of the present invention, more than one turbulating means 30 can also be included. Preferably, the turbulating means 30 will include a series of rotating veins 31 disposed within the flow through path 20 of the device 10 and functioning to agitate the fluid composition and thereby further effect its complete mixing. Accordingly, in one embodiment the turbulating means 30 can be included prior to and/or after initial influencing of the fluid composition by the magnetic means 40.

As an additional alternative, and because in some instances it may be necessary to further treat the fluid composition to more affectively provide for complete mixing and molecule organization, heating means 46 and/or sonic influencing means 48 can be included. For example, in one embodiment the heating 46 means can include a heating coil 47 or similar heating means which will substantially heat the fluid composition prior to and/or subsequent to the fluid composition's passage through the magnetic means 40. Similarly, the sonic influencing means 48 can be disposed to initiate a sonic influence on the fluid composition prior to and/or after the fluid composition is influenced by the magnetic means. Although many varieties of sonic influencing means can be utilized, in the preferred embodiment the sonic influencing means can be in the form of low frequency waves as through a transducer. Further, a similar sonic influencing means can be used when applying the treated mixture to the material mass.

Finally, because as previously recited, a carrier fluid may initially be magnetically influenced and a material to be delivered is added at a later point, the device 10 of the present invention can also include a secondary inlet 25. Preferably, the secondary inlet 25 will be disposed downstream of a preliminary magnetic means along the flow through path 20, and can be structured to permit the addition of a second material either in fluid, solid or gas form, depending the normal state of the second material. As such, the carrier fluid, often water, which has already been magnetically influenced so as to increase its own permeability and organization will be mixed with this second material in a substantially more effective and complete manner, often with the assistance of the turbulating means, prior to being cycled through the magnetic means 40 for appropriate organization of the molecules of the mixture as a whole.

It can be readily understood that there are a broad range of potential uses of the preferred embodiment of the method of the present invention. For example, this method can be used on metal objects, such as artifacts which have been salvaged from the ocean and become greatly weakened from long exposure to the seawater, making them susceptible to disintegration if exposed to normal environmental conditions outside of the water. Another use of this method would be to introduce chemicals into an object that is generally exposed to the elements for the purpose of sealing the object to make it substantially waterproof. Further, the method can be used to more effectively add nutrients to a plant or to a person.

The method of the present invention, therefore, has numerous applications where a substance must be effectively delivered into a material mass. Since many modifications, variations, and changes in detail can be made to the described preferred embodiment of the invention, it is intended that all matters in the foregoing description be interpreted as illustrative and not in a limiting sense. For example, the fluids that are subjected to the magnetic influences for subsequent introduction into the material mass may be the proprietary additives themselves if such additives are in fluid form, thereby eliminating the need for separate carrier fluids. Thus, the scope of the invention should be determined by the appended claims and their legal equivalents.

What is claimed is:

1. A method of delivering a substance into a material mass comprising the steps of:
    a) measuring at least one quantity of at least one liquid material to be delivered,
    b) applying a polarized magnetic field to said liquid material until fluid molecules of said liquid material are rearranged from a normal agglomerated state to a more linear and organized state, thereby increasing a permeability and effectiveness thereof, and
    c) introducing said magnetically influenced liquid material to the material mass for penetrating therein and direct, substantial absorbing of said magnetically influenced liquid material by the material mass.

2. A method of delivering a substance into a material mass comprising the steps of:
    a) measuring a quantity of a carrier fluid,
    b) measuring at least one quantity of at least one material to be delivered,
    c) mixing said quantity of said carrier fluid and said quantity of said material to be delivered,
    d) subjecting said mixture of said carrier fluid and said quantity of said material to be delivered to a polarizing magnetic influence until fluid molecules of said mixture are rearranged from a normal agglomerated state to a more linear and organized state such that a permeability and effectiveness thereof is increased, and
    e) introducing said mixture to the material mass for penetrating therein and direct, substantial absorbing of said mixture by the material mass.

3. A method of delivering a substance into a material mass as recited in claim 2, further comprising the step of subjecting said carrier fluid to a magnetic influence, prior to the step of measuring a quantity of a material to be delivered.

4. A method of delivering a substance into a material mass as recited in claim 3, further comprising the step of subjecting said carrier fluid to a turbulent influence, prior to the step of measuring a quantity of a material to be delivered.

5. A method of delivering a substance into a material mass as recited in claim 3, further comprising the step of subjecting said carrier fluid to a heating influence, prior to the step of measuring a quantity of a material to be delivered.

6. A method of delivering a substance into a material mass as recited in claim 3, further comprising the step of subjecting said carrier fluid to a sonic influence, prior to the step of measuring a quantity of a material to be delivered.

7. A method of delivering a substance into a material mass as recited in claim 2, wherein the step of subjecting said mixture of said carrier fluid and said quantity of said material to be delivered to a magnetic influence is repeated a plurality of times so as to have a cycling effect and substantially alter and align the fluid molecules of the mixture.

8. A method of delivering a substance into a material mass as recited in claim 2, further comprising the step of subjecting said mixture to a turbulent influence, prior to the step of subjecting said mixture of said carrier fluid and said quantity of said material to be delivered to a magnetic influence.

9. A method of delivering a substance into a material mass as recited in claim 2, further comprising the step of subjecting said mixture to a turbulent influence, after the step of subjecting said mixture of said carrier fluid and said quantity of said material to be delivered to a magnetic influence.

10. A method of delivering a substance into a material mass as recited in claim 2, further comprising the step of subjecting said mixture to a heating influence, prior to the step of subjecting said mixture of said carrier fluid and said quantity of said material to be delivered to a magnetic influence.

11. A method of delivering a substance into a material mass as recited in claim 2, further comprising the step of subjecting said mixture to a heating influence, after the step of subjecting said mixture of said carrier fluid and said quantity of said material to be delivered to a magnetic influence.

12. A method of delivering a substance into a material mass as recited in claim 2, further comprising the step of subjecting said mixture to a sonic influence, prior to the step of subjecting said mixture of said carrier fluid and said quantity of said material to be delivered to a magnetic influence.

13. A method of delivering a substance into a material mass as recited in claim 2, further comprising the step of subjecting said mixture to a sonic influence, after the step of subjecting said mixture of said carrier fluid and said quantity of said material to be delivered to a magnetic influence.

14. A device for the magnetic processing of a fluid substance to be delivered into a material mass, said device comprising:
    a fluid inlet structured to permit the introduction of a fluid composition therethrough,
    magnetic means structured and disposed to subject the fluid composition to a polarizing magnetic influence and thereby rearrange fluid molecules of said fluid composition from a normal agglomerated state to a more linear and organized state such that a permeability and effectiveness thereof is increased,
    recycling means structured and disposed to effect repeated subjecting of the fluid composition to said magnetic influence, and
    a fluid outlet.

15. A device as recited in claim 14 further including turbulating means structured and disposed to agitate said fluid composition.

16. A device as recited in claim 14 further including heating means structured and disposed to heat said fluid composition.

17. A device as recited in claim 14 further including sonic influencing means structured and disposed to initiate a sonic influence to effect said fluid composition.

18. A device as recited in claim 14 wherein said magnetic means includes a central axis wherethrough said fluid composition passes disposed in fluid flow communication with said fluid inlet, said magnetic means being structured to provide north and south magnetic fields and concentrate only one of said magnetic fields on said central axis so as to provide magnetic treatment of the fluid composition located generally along said central axis and within said one magnetic field.

19. A device as recited in claim 14 wherein said recycling means includes a plurality of said magnetic means disposed in line with one another.

20. A device as recited in claim 14 wherein said recycling means includes a pump structured to pump said fluid composition repeatedly through said magnetic means.

21. A device as recited in claim 14 further including a secondary inlet structured and disposed to permit the addition of a second material to said fluid composition for subsequent mixing and magnetic treatment thereof.

22. A device as recited in claim 14 wherein said turbulating means are structured to mix said fluid composition and said second material.

* * * * *